(12) United States Patent
Bengtsson et al.

(10) Patent No.: US 11,491,283 B2
(45) Date of Patent: Nov. 8, 2022

(54) NEEDLE UNIT WITH FLOATING NEEDLE HUB

(71) Applicant: Novo Nordisk A/S, Bagsvaerd (DK)

(72) Inventors: Henrik Bengtsson, Taastrup (DK); Vera Pinto Glenting, Copenhagen (DK); Kezia Ann Friis Praestmark, Koebenhavn N (DK); Bo Kvolsbjerg, Helsingoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/265,827

(22) PCT Filed: Aug. 9, 2019

(86) PCT No.: PCT/EP2019/071467
§ 371 (c)(1),
(2) Date: Feb. 4, 2021

(87) PCT Pub. No.: WO2020/030798
PCT Pub. Date: Feb. 13, 2020

(65) Prior Publication Data
US 2021/0379297 A1    Dec. 9, 2021

(30) Foreign Application Priority Data

Aug. 10, 2018 (EP) .................................. 18188538

(51) Int. Cl.
*A61M 5/32* (2006.01)

(52) U.S. Cl.
CPC ........ *A61M 5/3293* (2013.01); *A61M 5/3257* (2013.01); *A61M 5/3271* (2013.01); *A61M 2205/0205* (2013.01)

(58) Field of Classification Search
CPC .............. A61M 5/3293; A61M 5/3257; A61M 5/3271; A61M 2205/0205; A61M 2005/208; A61M 2005/3267; A61M 5/326; A61M 5/3243; A61M 5/32; A61M 5/34; A61M 5/321; A61M 5/20; A61M 2005/2073; A61M 5/178; A61M 5/001
See application file for complete search history.

(56) References Cited

U.S. PATENT DOCUMENTS

| 9,352,101 | B2 | 5/2016 | Roberts et al. |
| 9,789,264 | B2 | 10/2017 | Roberts et al. |
| 2003/0078546 | A1 | 4/2003 | Jensen |
| 2008/0167624 | A1* | 7/2008 | Weston ............... A61M 5/3202 604/198 |
| 2015/0273161 | A1* | 10/2015 | Bengtsson ............ A61M 5/326 604/198 |
| 2017/0106135 | A1* | 4/2017 | Bengtsson ............ A61M 5/326 |

FOREIGN PATENT DOCUMENTS

| WO | 2010139672 A1 | 12/2010 |
| WO | 2015062845 A1 | 5/2015 |
| WO | 2015150179 A1 | 10/2015 |
| WO | 2017114894 A1 | 7/2017 |

* cited by examiner

*Primary Examiner* — Bhisma Mehta
*Assistant Examiner* — Phoebe Anne Staton
(74) *Attorney, Agent, or Firm* — Wesley Nicolas

(57) ABSTRACT

The present invention provides a needle unit (10) for use with a pen injection device, wherein the needle unit (10) comprises a needle shield (50) and an axially movable needle hub (25).

17 Claims, 3 Drawing Sheets

NEEDLE UNIT WITH FLOATING NEEDLE HUB

CROSS-REFERENCE TO RELATED APPLICATIONS

This application is a 35 U.S.C. § 371 National Stage application of International Application PCT/EP2019/071467 (published as WO 2020/030798), filed Aug. 9, 2019, which claims priority to European Patent Application 18188538.5, filed Aug. 10, 2018; the contents of which are incorporated herein by reference.

FIELD OF THE INVENTION

The present invention relates generally to medical devices and more particularly to needle units for use with drug delivery devices.

BACKGROUND OF THE INVENTION

Many drugs must be administered parenterally to be effective in the body and some of these, e.g. insulin and glp-1, may require one or more doses to be delivered subcutaneously on a daily basis. Subcutaneous drug delivery is often associated with discomfort as many people dislike the thought of having an injection needle inserted through the skin. An undisclosed number of people even suffer from needle-phobia, and these people often benefit from using needle units with shielded needles, where the injection needle remains out of sight during handling of the needle unit, including insertion of the injection needle into the skin.

Typically, this type of needle unit comprises an axially movable sheath which can be slid between a first position in which it covers the injection needle and a second position in which the injection needle is exposed and ready for injection. In some cases the sheath is spring loaded such that it is automatically slid back to the first position when the injection needle is retracted from the skin. An example of this is disclosed in US 2003/0078546 (Jensen).

Needle units are typically wrapped and sealed individually to ensure sterility prior to use. In connection with a dose administration action the user must therefore unwrap the needle unit, mount it on the injection device, perform the injection, dismount it from the injection device, re-wrap or otherwise encapsulate it to prevent needle stick injuries, and finally dispose of it, preferably in a dedicated sharps container.

The readying and subsequent removal of the needle unit is both the most complicated and the most time-consuming part of the injection procedure. Especially for young and elderly users the handling of the small items and foils can present a challenge and make the task of injection a bit cumbersome. As a result, some users reuse the needle unit several times. In fact, some users only change the needle unit when the injection device is empty, or if the needle for example exhibits clogging or hooking. This reduces the number of times these users have to carry out needle handling activities significantly.

However, it also entails increased risks of both infections and needle stick injuries, the former due to needle contamination and the latter due to the users typically disposing of the original needle unit packaging in connection with the fitting of the needle, why this packaging is not available as receptacle when they change the needle unit after several times of reuse.

WO 2015/062845 (Novo Nordisk A/S) discloses a needle unit for a pen injection device where a portion of the front needle is housed between injections in a reservoir holding a preservative containing liquid. This portion of the front needle is thus cleaned by, and stored in, the preservative containing liquid following each injection action, thereby reducing the risk of microbial contamination. The preservative containing liquid is identical to the drug present in the cartridge and is transferred from the cartridge to the reservoir in connection with a first use of the injection device.

In both of the above types of needle units the injection needle is hidden by a shield with a seal and only protrudes the seal during insertion into the skin. This reduces the user's awareness of the pointed needle which tends to lead to a reduced sensation of pain. However, it also prevents the user from verifying that the needle tip is actually properly inserted. With such needle units there is a risk that the skin portion around the injection site, during displacement of the needle shield, deflects and forms a cavity in which the needle tip can rest without penetrating the epidermis. This will lead to a so-called wet-shot, where the dose of drug is undesirably expelled onto the surface of the skin instead of into the body.

SUMMARY OF THE INVENTION

It is an object of the invention to eliminate or reduce at least one drawback of the prior art, or to provide a useful alternative to prior art solutions.

In particular, it is an object of the invention to provide a needle unit where the injection needle remains out of sight both during an injection and between injections, yet where proper injection needle insertion is ensured.

It is another object of the invention to provide such a needle unit which is simple, easy to operate, and which requires few handling steps.

It is a further object of the invention to provide an injection system employing such a needle unit.

In the disclosure of the present invention, aspects and embodiments will be described which will address one or more of the above objects and/or which will address objects apparent from the following text.

In one aspect the invention provides a needle unit according to claim 1.

Accordingly, a needle unit for use with a pen injection device is provided. The needle unit comprises a base member adapted to be attached to, e.g. mounted on, a needle mount of the pen injection device. The base member extends along a longitudinal axis and comprises an interiorly arranged attachment portion which defines a proximal receiving space and which is configured for reception and retention of the needle mount.

The needle unit further comprises a needle hub, which is coupled with the base member distally of the interior attachment portion, an injection needle which is fixedly mounted in the needle hub and which comprises a distal needle end portion intended for insertion through a skin barrier, and a proximal needle end portion extending into the proximal receiving space for permanent residence therein, and a needle shield arranged exteriorly of the needle hub. The needle shield comprises an axially extending wall and is axially displaceable relative to the base member between an extended position and an intermediate position and further between the intermediate position and a maximum displaced position. A first bias structure biases the needle shield towards the extended position.

The needle hub is axially reciprocatable relative to the base member between a proximal needle hub position and a distal needle hub position. A second bias structure, acting between the base member and the needle hub, biases the needle hub towards the distal needle hub position.

During axial displacement from the extended position to the intermediate position the needle shield undergoes relative motion with respect to the needle hub from a needle covering relative position in which the distal needle end portion is surrounded by the axially extending wall to a needle exposing relative position in which the distal needle end portion extends distally beyond the axially extending wall. During axial displacement from the intermediate position to the maximum displaced position the needle shield undergoes joint motion with the needle hub which brings the needle hub from the distal needle hub position to the proximal needle hub position. Said joint motion may for example be due to a contact between the needle shield and the needle hub, e.g. a distal surface of the needle hub, established in the intermediate position.

The degree of exposure of the injection needle is thus determined by the relative axial position of the needle hub and the needle shield. In conventional prior art needle units the distal needle end portion is fully exposed only when the needle shield is fully displaced, or when it is not possible in practice to displace the needle shield further. However, in the present needle unit construction, where the needle hub is arranged floatingly in the base member, the distal needle end portion is fully exposed before the needle shield is fully displaced, and to obtain full needle shield displacement a user needs to overcome an additional force from the second bias structure. The user is thus encouraged to increase the pressure and cause further displacement of the needle shield in an effort to reach an apparent desired end state of the needle insertion, at a point where the distal needle end portion is already fully exposed.

Hence, the user actually uses more than adequate force in order to accomplish the needle insertion, and the additional force applied to the injection pen together with the additional travel of the needle shield, performed jointly with the needle hub, provides for an increased contact pressure between the needle unit and the skin surface, which eliminates the risk of cavity formation and results in a proper positioning of the distal needle end portion within the skin.

The needle shield may comprise an interior chamber structure holding an antibacterial substance, and the distal needle end portion may reside in the antibacterial substance when the needle shield is in the extended position. The distal needle end portion is thereby cleaned after an injection and maintained in a biostatic environment between injections, allowing for safe multiple reuse of the needle unit with an ensuing reduction of needle unit disposals.

In some embodiments of the invention the antibacterial substance comprises an antibacterial rubber plug which the distal needle end is then ejected from during injection procedures and retracted back into after completed injection.

In other embodiments of the invention the antibacterial substance comprises a preservative containing liquid drug, e.g. identical to the one held by the pen injection device.

The pen injection device may be adapted to hold a drug reservoir of the cartridge type having a penetrable self-sealing septum. The penetrable self-sealing septum is then positioned at a distal end portion of the needle mount such that when the base member is mounted over the needle mount the proximal needle end portion in the proximal receiving space transpierces the penetrable self-sealing septum to establish fluid communication with an interior of the drug reservoir. Because the proximal needle end portion is positioned in the proximal receiving space both when the needle hub is in the proximal needle hub position and in the distal needle hub position the fluid communication between the interior of the drug reservoir and the injection needle remains uninterrupted even if the needle unit is reused. The penetrable self-sealing septum does therefore not need be repeatedly penetrated in connection with multiple reuses of the needle unit. It is desirable to avoid multiple penetrations of such a septum because at each penetration there is a risk that coring of the septum will occur. Furthermore, if the interior of the drug reservoir is filled, or substantially filled, with a preservative containing liquid drug the uninterrupted fluid communication will ensure establishment of a bacteria hostile internal environment positively contributing to keeping the needle interior clean.

The first bias structure may comprise a first compression spring, acting between the base member and the needle shield. The second bias structure may comprise a second compression spring. The user must then overcome firstly the biasing force from the first compression spring to effect the displacement of the needle shield from the extended position to the intermediate position, in which the distal needle end portion is fully exposed, and secondly the combined biasing force from the first compression spring and the second compression spring to obtain a full needle shield displacement.

An exterior surface portion of the needle hub may comprise a longitudinal hub track, and the base member may further comprise an inner section carrying a radially inwardly directed inner section protrusion adapted to travel the longitudinal hub track between a proximal hub track end and a distal hub track end, a position of the radially inwardly directed inner section protrusion at the proximal hub track end defining the distal needle hub position, and a position of the radially inwardly directed inner section protrusion at the distal hub track end defining the proximal needle hub position. This provides for a very simple construction where the possible movements of the floating needle hub relative to the base member are well-defined.

An exterior surface portion of the needle shield may comprise a longitudinal shield track, and the base member may further comprise an outer section carrying a radially inwardly directed outer section protrusion adapted to travel the longitudinal shield track between a proximal shield track end and a distal shield track end, a position of the radially inwardly directed outer section protrusion at the proximal shield track end defining the extended position, and a position of the radially inwardly directed outer section protrusion at the distal shield track end defining the maximum displaced position. Similarly to the above, this provides for a very simple way of defining the possible movements of the needle shield relative to the base member.

The interior attachment portion may form part of the inner section, and the inner section may further comprise a transversal partition adjacent a distal end section of the interior attachment portion, the transversal partition comprising a through-going bore for slidable reception of the injection needle. This establishes a well-defined axial position of the needle mount relative to the base member following attachment of the needle unit on the pen injection device and thereby provides for a predetermined axial position of a drug reservoir carried by the pen injection device relative to the proximal needle end portion, allowing an optimised and uniformised extent of protrusion of proximal needle end portions into respective drug reservoirs, relevant for minimising drug residuals in the various drug reservoirs.

In another aspect the invention provides an injection system comprising a needle unit as described in the above and a pen injection device comprising a needle mount. The needle mount and the interior attachment portion may be configured for releasable interengagement, e.g. in case the pen injection device is of the durable device type, or may be permanently engaged, e.g. in case the pen injection device is of the prefilled disposable device type. In case of the latter the lifetime of the needle unit equals the lifetime of the pen injection device.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "upwards" and "downwards" and "left" and "right", are used, these refer to the appended figures and not necessarily to an actual situation of use. The shown figures are schematic representations for which reason the configuration of the different structures as well as their relative dimensions are intended to serve illustrative purposes only.

Figure 1:
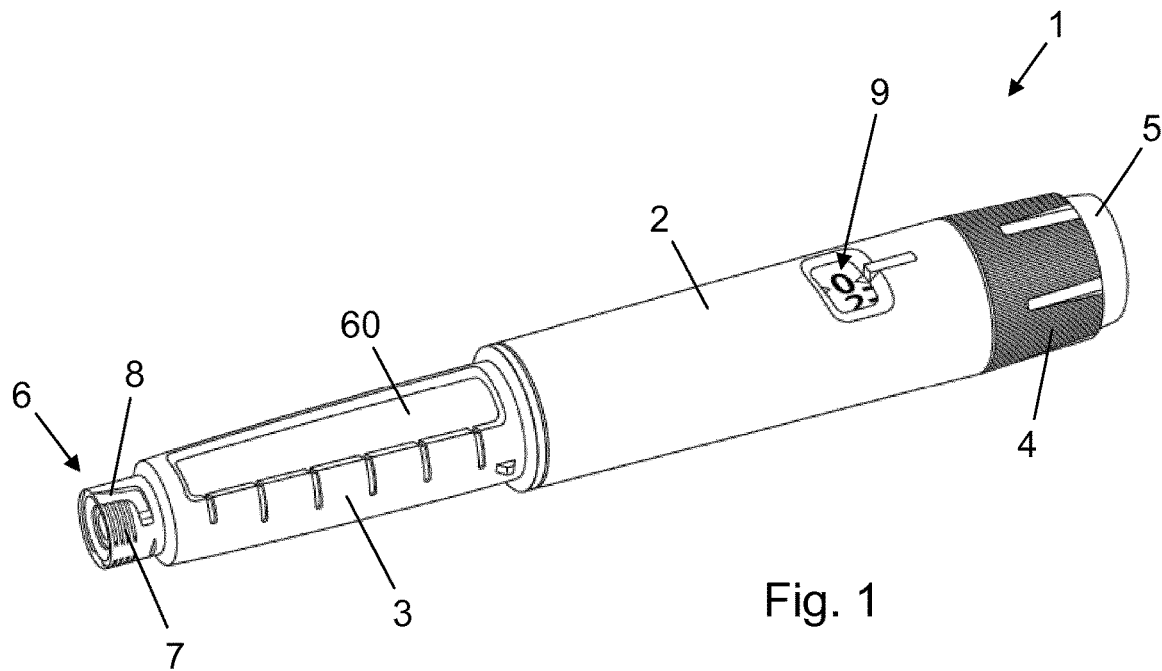
FIG. 1 is a perspective view of an exemplary injection device to which a needle unit according to the present invention may be attached.

FIG. 1 is a perspective view of an exemplary injection pen 1 to which a needle unit according to the present invention may be attached. The injection pen 1 has a longitudinal housing 2 which accommodates an injection mechanism (not visible). A cartridge holder 3 is attached to a distal end portion of the housing 2 and supports a cartridge 60 holding a liquid drug. At its own distal end the cartridge holder 3 is provided with a needle mount 6 configured to receive and retain a needle unit carrying an injection needle. The needle mount 6 comprises both a male thread 7 and a bayonet track 8, superposed onto the male thread 7, so as to be compatible with needle units having a thread interface as well as needle units having a bayonet interface.

In the present case the cartridge holder 3 is fixedly attached to the housing 2, as the injection pen 1 is of the so-called prefilled injection device type. However, in other cases the cartridge holder 3 could be detachably attached. In conventional fashion the injection pen 1 has, arranged at a proximal end portion thereof, a dose dial button 4 for selective setting of a dose to be delivered and an injection button 5 for actuation of the injection mechanism, and a currently set dose can be viewed through a window 9 in the housing 2. Non-exhaustive examples of injection devices which may be used with a needle unit as presented in the following are FlexTouch® and FlexPen®, manufactured by Novo Nordisk A/S.

Figure 2:
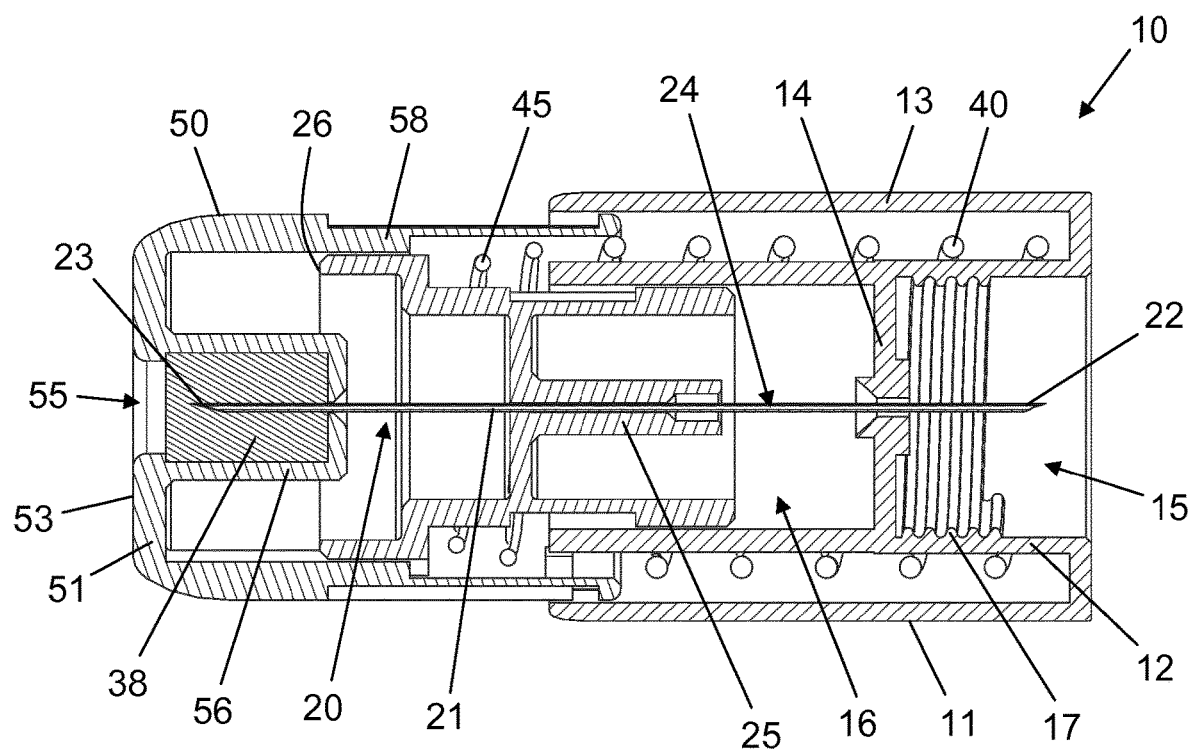
FIG. 2 is a longitudinal section view of a needle unit according to an embodiment of the invention.

FIG. 2 is a longitudinal section view of a needle unit 10 according to an embodiment of the invention in a pre-use state. The needle unit 10 has a base member 11 comprising an inner section 12 and an outer section 13. A transversal partition 14 divides the inner section 12 to provide a proximal receiving space 15 and a distal receiving space 16. A portion of the inner section 12 in the proximal receiving space 15 carries a female thread 17 for mating connection with the male thread 7 of the needle mount 6. The needle unit 10 further comprises a needle hub 25, carrying an injection needle 20 which extends along a general longitudinal axis, and a needle shield 50. The needle hub 25 is axially slidably arranged in the distal receiving space 16.

The injection needle 20 comprises an elongated needle tube 21 having a lumen 24, a proximal needle end 22 which is configured for penetration of a cartridge septum and residence in a cartridge interior, and a distal needle end 23 configured for insertion through the skin of the user. The needle tube 21 is fixedly mounted in the needle hub 25.

The needle shield 50 comprises a circumferential side wall 58, a transversal end wall 51, having a contact surface 53 for abutment with a skin portion surrounding the injection site and a central orifice 55, and an interior chamber structure 56 which carries an antibacterial plug 38 of rubber. The antibacterial plug 38 has a free distal end which is exposed to the surroundings via the orifice 55.

A shield spring 40, in the form of a compression spring, is arranged to act between the base member 11 and the needle shield 50, and a hub spring 45, also in the form of a compression spring, is arranged to act between the base member 11 and the needle hub 25.

In the depicted pre-use state of the needle unit 10 a distal portion of the needle tube 21, including the distal needle end 23, resides within the antibacterial plug 38, having gained access thereto via a proximal opening in the chamber structure 56, and a proximal portion of the needle tube 21, including the proximal needle end 22, resides within the receiving space 15, having gained access thereto via a bore in the transversal partition 14.

Figure 3:
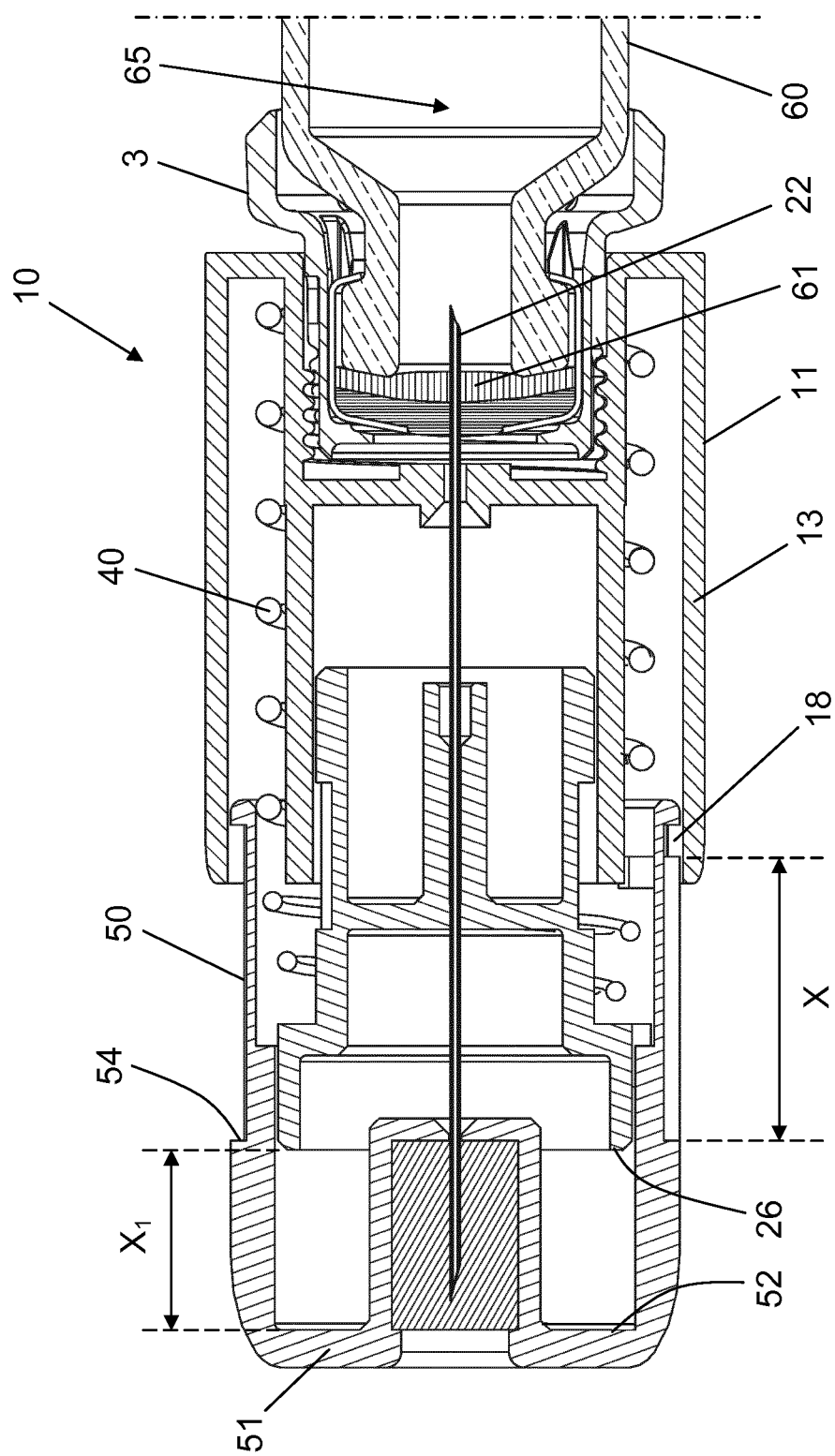
FIG. 3 is a longitudinal section view of the needle unit with an attached drug cartridge.
Figure 5:
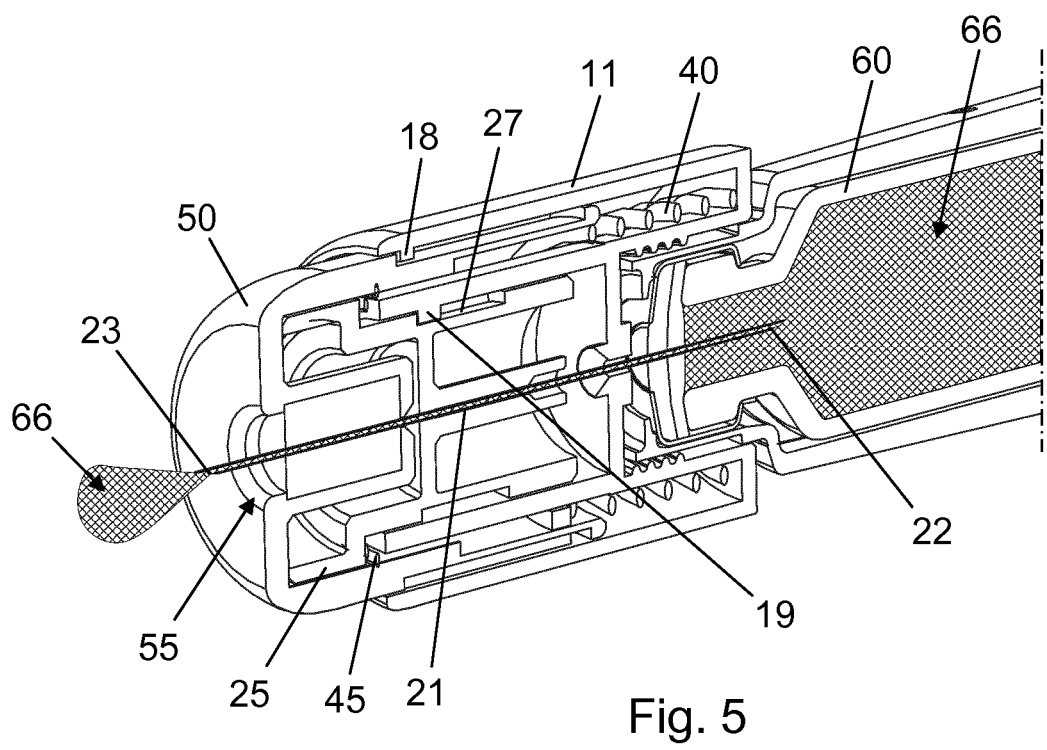
FIG. 5 is a longitudinally sectioned perspective view of the needle unit and the drug cartridge in a second in-use state, during drug injection.

FIG. 3 shows the needle unit 10 in a situation where the proximal receiving space 15 is occupied by a head portion of the cartridge 60 and the needle mount 6 of the cartridge holder 3, the male thread 7 being mated with the female thread 17. In this position of the cartridge holder 3 the proximal needle end 22 has penetrated a self-sealing cartridge septum 61 at the distal end of the cartridge 60, and a proximal end portion of the needle tube 21 thus extends from the cartridge septum 61 into a cartridge interior 65, establishing fluid communication with a liquid drug 66 (ref. FIG. 5) therein.

The needle shield 50 and the needle hub 25 are capable of relative axial motion between a needle covering relative position (shown in FIG. 3) in which the distal needle end 23 is accommodated within the antibacterial plug 38 and a needle exposing relative position (shown in FIG. 4) in which the distal needle end 23 protrudes from the antibacterial plug 38 through the orifice 55. In the needle covering relative position a distal rim 26 of the needle hub 25 and an inner surface 52 of the end wall 51 are spaced apart a distance, $X_1$, which reflects the extent of possible relative axial motion between the needle shield 50 and the needle hub 25.

Further, the needle shield 50 and the base member 11 are capable of relative axial motion between a fully extended relative position (shown in FIG. 3), in which the needle shield 50 and the needle hub 25 are in the needle covering relative position, and a fully displaced relative position (shown in FIG. 5). The shield spring 40 biases the needle shield 50 and the needle hub 25 towards the fully extended relative position.

In the fully extended relative position a proximally facing circumferential ledge 54 of the needle shield 50 and a distal face of an outer section protrusion 18 of the base member 11 are spaced apart a distance, X, which reflects the extent of possible relative axial motion between the needle shield 50 and the base member 11. Notably, $X>X_1$.

Figure 4:
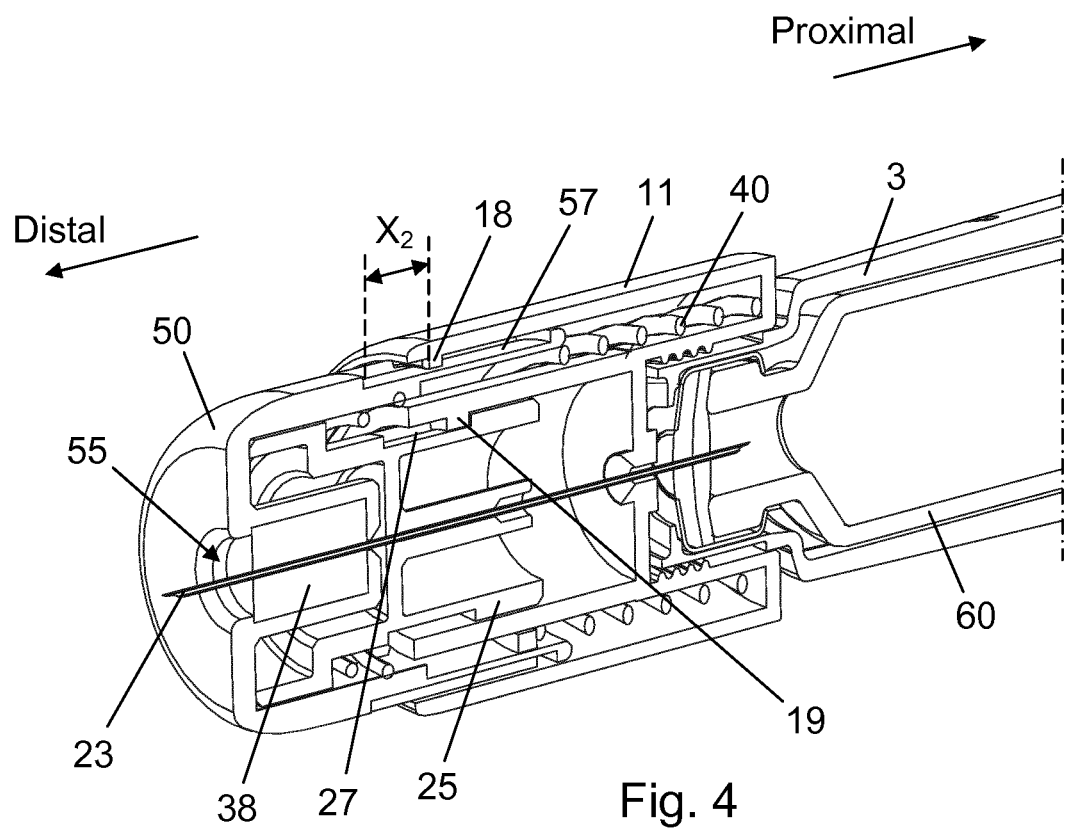
FIG. 4 is a longitudinally sectioned perspective view of the needle unit and the drug cartridge in a first in-use state, during insertion of the injection needle into the skin.

FIG. 4 is a longitudinally sectioned perspective view of the needle unit 10 and the cartridge 60 during insertion of the injection needle 20 into the skin (not shown). In the depicted state of the needle unit 10 the needle shield 50 and the base member 11 are in an intermediate relative position between the fully extended relative position and the fully displaced relative position in which the distal rim 26 of the needle hub 25 and the inner surface 52 of the end wall 51 have just been brought into contact, i.e. where the needle shield 50 and the needle hub 25 have been brought to the needle exposing relative position and where further converging motion between the needle shield 50 and the needle hub 25 is prevented.

During the relative axial motion between the needle shield 50 and the base member 11 that brings the two from the fully extended relative position to the intermediate position the outer section protrusion 18 travels along a longitudinal shield track 57, and the distance between the proximally facing circumferential ledge 54 and the distal face of the outer section protrusion 18 is thereby eventually reduced from X to $X_2$.

At this point the distal needle end 23 protrudes through the orifice 55 in correspondence with the desired needle insertion depth. Nevertheless, the needle shield 50 and the base member 11 are capable of further relative axial motion until the fully displaced relative position is reached. Also, the needle hub 25 and the base member 11 are capable of relative axial motion, against a biasing force from the hub spring 45. The extent of said motion is defined by the travel of an inner section protrusion 19 of the base member 11 along a longitudinal hub track 27 from a proximal hub track end (at which it is situated in FIG. 4) to a distal hub track end (at which it is situated in FIG. 5).

FIG. 5 shows the needle unit 10 and the cartridge 60 in a state where the needle shield 50 and the base member 11 are in the fully displaced relative position and an injection of a dose of the liquid drug 66 has commenced.

In summary, describing a situation of use where the needle unit 10 is already mounted on the needle mount 6, when an injection is needed the contact surface 53 is placed against a skin portion of the user and the injection pen 1 is pressed towards the skin. This action causes a relative axial motion between the base member 11 and the needle shield 50, which compresses the shield spring 50. Initially, the needle hub 25 remains stationary relative to the base member 11, being biased distally by the hub spring 45 while the inner section protrusion 19 at the proximal hub track end prevents distal motion of the needle hub 25 relative to the inner section 12.

Hence, during the first part of the relative axial motion between the base member 11 and the needle shield 50, which takes the base member 11 and the needle shield 50 from the fully extended relative position to the intermediate relative position, the needle shield 50 also undergoes relative axial motion with respect to the needle hub 25, said relative axial motion bringing the needle shield 50 and the needle hub 25 from the needle covering relative position to the needle exposing relative position.

In the needle exposing relative position, the transversal end wall 51 abuts the distal rim 26, and the distal needle end 23 protrudes through the orifice 55 a distance corresponding to the intended insertion depth in the skin. However, at this point the user cannot know if the distal needle end 23 has actually reached the intended insertion depth, as the entire injection needle 20 is hidden from the user's eyesight behind the base member 11, the needle shield 50, and the skin surface. The skin surface may in fact have deformed undesirably to produce a cavity around the orifice 55, such that only a portion of the distal needle end 23 has penetrated the skin, or may be even such that the distal needle end 23 has not penetrated the skin at all. Obviously, this situation is unfortunate, as a proper injection treatment requires a proper deposition of the drug in the skin.

However, the particular construction of the needle unit 10 urges the user to press the injection pen 1 further towards the skin in order to eliminate the visible gap, $X_2$, between the proximally facing circumferential ledge 54 and the distal face of the outer section protrusion 18, which gives the impression that the needle shield 50 is not sufficiently depressed. This causes a further relative axial motion between the base member 11 and the needle shield 50 towards the fully displaced relative position, although now the needle shield 50 slaves the needle hub 25 which then also undergoes relative axial motion with respect to the base member 11.

Thus, the relative axial motion between the base member 11 and the needle shield 50 from the intermediate relative position to the fully displaced relative position occurs against the force from the shield spring 40 but also against the additional force from the hub spring 45, requiring an extra effort from the user. Notably, since the needle shield 50 and the needle hub 25 do not undergo any relative axial motion at this stage the position of the distal needle end 23 relative to the transversal end wall 51 does not change. In other words, the needle shield 50 and the needle hub 25 remain in the needle exposing relative position as the base member 11 and the needle shield 50 undergo relative motion from the intermediate relative position to the fully displaced relative position. The proximal needle end 22, however, is moved further into the cartridge interior 65 due to the needle hub 25 being displaced proximally in the distal receiving space 16.

The fact that the needle unit 10 comprises a spring loaded over-travel feature for the needle shield 50, and that the user must apply a total compression force which exceeds the compression force needed to expose the distal needle end 23 in order to seemingly obtain a sufficient displacement of the needle shield 50, ensures that the needle unit 10 maintains full contact with the skin during the injection procedure, thereby eliminating the risk of skin pocket generation and providing for a proper insertion of the distal needle end 23.

When the inner section protrusion 19 reaches the distal hub track end further converging relative axial motion between the needle hub 25 and the base member 11 is prevented, as is further converging relative axial motion between the base member 11 and the needle shield 50. The base member 11 and the needle shield 50 are now in the fully displaced relative position, and the distal needle end 23 is properly positioned in the skin. The user can therefore operate the injection button 5 to initiate the injection of the set dose well aware that the dose will be administered to the intended body compartment.

After completed dose administration the user withdraws the injection needle 20 from the skin by simply pulling back the injection pen 1. The hub spring 45 will thereby return the needle hub 25 to the position where the inner section protrusion 19 abuts the proximal hub track end, and the shield spring 40 will ensure that the base member 11 and the needle shield 50 return to the fully extended relative position. The distal needle end 23 is thereby returned to the interior chamber structure 56 where it will reside within the antibacterial plug 38.

The antibacterial plug 38 will disinfect the distal needle end 23 after the injection such that the injection needle 20 may be safely reused for one or more subsequent injection(s). The needle unit 10 can therefore remain on the injection pen 1, with the female thread 17 and the male thread 7 in interengagement, between injections, thus reducing the number of required needle handling actions.

The invention claimed is:

1. A needle unit for use with a pen injection device, comprising:
    a base member for attachment to a needle mount of the pen injection device, the base member extending along a main axis and comprising an interior attachment portion defining a proximal receiving space and being configured for reception and retention of the needle mount,
    a needle hub coupled with the base member distally of the interior attachment portion,
    an injection needle fixedly mounted in the needle hub and comprising a distal needle end portion intended for insertion through a skin barrier, and a proximal needle end portion extending into the proximal receiving space and permanently residing therein,
    a needle shield arranged exteriorly of the needle hub and comprising an axially extending wall, the needle shield being axially displaceable relative to the base member between an extended position and an intermediate position and further between the intermediate position and a maximum displaced position, and
    a first bias structure biasing the needle shield towards the extended position,
wherein the needle hub is axially reciprocatable relative to the base member between a proximal needle hub position and a distal needle hub position, the needle hub being biased towards the distal needle hub position by a second bias structure which acts between the base member and the needle hub,
wherein during axial displacement from the extended position to the intermediate position the needle shield undergoes relative motion with respect to the needle hub from a needle covering relative position in which the distal needle end portion is surrounded by the axially extending wall to a needle exposing relative position in which the distal needle end portion extends distally beyond the axially extending wall,
wherein during axial displacement from the intermediate position to the maximum displaced position the needle shield undergoes joint motion with the needle hub which brings the needle hub from the distal needle hub position to the proximal needle hub position,
wherein an exterior surface portion of the needle shield comprises a longitudinal shield track, and
wherein the base member further comprises an outer section carrying a radially inwardly directed outer section protrusion adapted to travel the longitudinal shield track between a proximal shield track end and a distal shield track end, a position of the radially inwardly directed outer section protrusion at the proximal shield track end defining the extended position, and a position of the radially inwardly directed outer section protrusion at the distal shield track end defining the maximum displaced position.

2. A needle unit according to claim 1, wherein the needle shield comprises an interior chamber structure holding an antibacterial substance, and
    wherein the distal needle end portion resides in the antibacterial substance when the needle shield is in the extended position.

3. A needle unit according to claim 2, wherein the antibacterial substance comprises an antibacterial rubber plug.

4. A needle unit according to claim 2, wherein the antibacterial substance comprises a liquid drug containing a preservative.

5. A needle unit according to claim 1, wherein the first bias structure comprises a first compression spring, acting between the base member and the needle shield, and the second bias structure comprises a second compression spring.

6. A needle unit according to claim 1, wherein an exterior surface portion of the needle hub comprises a longitudinal hub track, and
wherein the base member further comprises an inner section carrying a radially inwardly directed inner section protrusion adapted to travel the longitudinal hub track between a proximal hub track end and a distal hub track end, a position of the radially inwardly directed inner section protrusion at the proximal hub track end defining the distal needle hub position, and a position of the radially inwardly directed inner section protrusion at the distal hub track end defining the proximal needle hub position.

7. A needle unit according to claim 6, wherein the interior attachment portion forms part of the inner section, and wherein the inner section further comprises a transversal partition adjacent a distal end section of the interior attachment portion, the transversal partition comprising a through-going bore for slidable reception of the injection needle.

8. An injection system comprising the needle unit according to claim 1 and the pen injection device comprising the needle mount, wherein the needle mount and the interior attachment portion are configured for releasable interengagement.

9. An injection system comprising the needle unit according to claim 1 and the pen injection device comprising the needle mount, wherein the needle mount is permanently engaged with the interior attachment portion.

10. A needle unit for use with a pen injection device, comprising:
- a base member for attachment to a needle mount of the pen injection device, the base member extending along a main axis and comprising an interior attachment portion defining a proximal receiving space and being configured for reception and retention of the needle mount,
- a needle hub coupled with the base member distally of the interior attachment portion,
- an injection needle fixedly mounted in the needle hub and comprising a distal needle end portion intended for insertion through a skin barrier, and a proximal needle end portion extending into the proximal receiving space and permanently residing therein,
- a needle shield arranged exteriorly of the needle hub and comprising an axially extending wall, the needle shield being axially displaceable relative to the base member between an extended position and an intermediate position and further between the intermediate position and a maximum displaced position, and
- a first bias structure biasing the needle shield towards the extended position, wherein the needle hub is axially reciprocatable relative to the base member between a proximal needle hub position and a distal needle hub position, the needle hub being biased towards the distal needle hub position by a second bias structure which acts between the base member and the needle hub, wherein during axial displacement from the extended position to the intermediate position the needle shield undergoes relative motion with respect to the needle hub from a needle covering relative position in which the distal needle end portion is surrounded by the axially extending wall to a needle exposing relative position in which the distal needle end portion extends distally beyond the axially extending wall, and wherein during axial displacement from the intermediate position to the maximum displaced position the needle shield undergoes joint motion with the needle hub which brings the needle hub from the distal needle hub position to the proximal needle hub position, and wherein the base member further comprises an inner section carrying a radially inwardly directed inner section protrusion adapted to travel a longitudinal hub track between a proximal hub track end and a distal hub track end, a position of the radially inwardly directed inner section protrusion at the proximal hub track end defining the distal needle hub position, and a position of the radially inwardly directed inner section protrusion at the distal hub track end defining the proximal needle hub position, and wherein the interior attachment portion forms part of the inner section, and wherein the inner section further comprises a transversal partition adjacent a distal end section of the interior attachment portion, the transversal partition comprising a through-going bore for slidable reception of the injection needle.

11. A needle unit according to claim 10, wherein the needle shield comprises an interior chamber structure holding an antibacterial substance, and
- wherein the distal needle end portion resides in the antibacterial substance when the needle shield is in the extended position.

12. A needle unit according to claim 11, wherein the antibacterial substance comprises an antibacterial rubber plug.

13. A needle unit according to claim 11, wherein the antibacterial substance comprises a preservative containing liquid drug.

14. A needle unit according to claim 10, wherein the first bias structure comprises a first compression spring, acting between the base member and the needle shield, and the second bias structure comprises a second compression spring.

15. A needle unit according to claim 10, wherein an exterior surface portion of the needle hub comprises the longitudinal hub track.

16. An injection system comprising the needle unit according to claim 10 and the pen injection device comprising the needle mount, wherein the needle mount and the interior attachment portion are configured for releasable interengagement.

17. An injection system comprising the needle unit according to claim 10 and the pen injection device comprising the needle mount, wherein the needle mount is permanently engaged with the interior attachment portion.

\* \* \* \* \*